United States Patent
Shimizu et al.

(10) Patent No.: US 8,105,626 B2
(45) Date of Patent: Jan. 31, 2012

(54) GRANULES CONTAINING ACID-UNSTABLE CHEMICAL IN LARGE AMOUNT

(75) Inventors: Toshihiro Shimizu, Itami (JP); Yoshinori Nakano, Takarazuka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1442 days.

(21) Appl. No.: 10/492,690

(22) PCT Filed: Oct. 16, 2002

(86) PCT No.: PCT/JP02/10720
§ 371 (c)(1),
(2), (4) Date: Apr. 15, 2004

(87) PCT Pub. No.: WO03/032953
PCT Pub. Date: Apr. 24, 2003

(65) Prior Publication Data
US 2005/0003005 A1    Jan. 6, 2005

(30) Foreign Application Priority Data

Oct. 17, 2001   (JP) .................................. 2001-319444

(51) Int. Cl.
*A61K 9/24*     (2006.01)
*A61K 9/14*     (2006.01)
*A61K 31/44*    (2006.01)

(52) U.S. Cl. ..................... 424/471; 424/489; 514/338

(58) Field of Classification Search .................. 424/471, 424/489; 514/338
See application file for complete search history.

(56) References Cited

U.S. PATENT DOCUMENTS

| | | | | |
|---|---|---|---|---|
| 4,853,230 | A | 8/1989 | Lovgren et al. | 424/466 |
| 6,328,994 | B1 | 12/2001 | Shimizu et al. | 424/489 |
| 2002/0039597 | A1 | 4/2002 | Ukai et al. | 424/490 |

FOREIGN PATENT DOCUMENTS

| | | |
|---|---|---|
| EP | 0 237 200 | 9/1987 |
| EP | 0 277 741 | 8/1988 |
| EP | 0 642 797 | 3/1995 |
| EP | 1 108 425 | 6/2001 |
| GB | 2 189 698 | 11/1987 |
| JP | 5-139964 | 6/1993 |
| JP | 5-255088 | 10/1993 |
| JP | 7-223956 | 8/1995 |
| JP | 9-502740 | 3/1997 |
| JP | 10-36290 | 2/1998 |
| JP | 11-501949 | 2/1999 |
| JP | 11-139960 | 5/1999 |
| JP | 2000-212085 | 8/2000 |
| JP | 2000-302681 | 10/2000 |
| JP | 2000-355540 | 12/2000 |
| WO | 95/01783 | 1/1995 |
| WO | 96/01624 | 1/1996 |
| WO | 97/25065 | 7/1997 |
| WO | 99/25323 | 5/1999 |
| WO | 99/27917 | 6/1999 |
| WO | WO 99/38513 * | 8/1999 |
| WO | 99/59544 | 11/1999 |
| WO | 00/06126 | 2/2000 |

OTHER PUBLICATIONS

Notice of Reasons for Rejection mailed Mar. 2, 2010 in corresponding Japanese Patent Application No. 2006-203539 (with English translation).
Extended European Search Report issued Sep. 13, 2011 in corresponding European Patent Application No. 10178017.9.

* cited by examiner

*Primary Examiner* — Robert A Wax
*Assistant Examiner* — Aradhana Sasan
(74) *Attorney, Agent, or Firm* — Wenderoth, Lind & Ponack, L.L.P.

(57) ABSTRACT

It is intended to provide preparations such as capsules containing an acid-unstable medicament (in particular, a benzimidazole compound having an antiulcer effect, etc.) at a high concentration which are prepared by using about 12% by weight or more (based on the total granules) of the acid-unstable chemical and blending a basic inorganic salt therewith to give granules of about 600 μm or more in the average particle size.

18 Claims, No Drawings

GRANULES CONTAINING ACID-UNSTABLE CHEMICAL IN LARGE AMOUNT

This application is a U.S. national stage of International Application No. PCT/JP02/10720 filed Oct. 16, 2002.

TECHNICAL FIELD

The present invention relates to stabilized granules, which comprises a high content of an acid-unstable medicament, in particular, a benzimiadzole compound useful as an antiulcer agent and a basic inorganic substance.

BACKGROUND ART

Since benzimidazole compounds such as lansoprazole, omeprazole and rabeprazole have gastric acid secretion inhibitory activity, gastric mucoca protecting activity, etc., they are widely used as a peptic ulcer treating agent.

However, these compounds are inferior in stability, and are unstable to humidity, temperature and light. In particular, they are unstable to acids and, when formulated into an aqueous solution or a suspension, they become extremely unstable with lowering of pH.

In addition, stability in the form of preparations, i.e., tablets, powders, fine granules, capsules, etc. becomes lower than that of the compounds alone because of their strong interaction with other components in formulated preparations, and color change or degradation is observed upon production or storage of the preparations. In order to stabilize them, JP 62-277322 A discloses enteric granules, enteric fine granules, etc. obtained by blending a stabilizing agent composed of a basic inorganic salt of magnesium and/or calcium, followed by enteric coating.

Meanwhile, it is necessary to apply an enteric coating to a benzimidazole compound because the compound has such properties that it is hardly soluble in water and is unstable to acids. An enteric coating does not dissolve in a stomach containing a relatively larger amount of water, but dissolves in a small intestine containing a smaller amount of water, whereby a benzimidazole compound is dissolved and absorbed. That is, since a composition containing a benzimidazole compound is required to be rapidly disintegrated in a small intestine, granules which have a larger surface area, and which are more easily and rapidly disintegrated or dissolved than tablets are considered to be more desired.

In Examples specifically disclosed in JP 62-277322 A, the content of benzimidazole compound is about 6.3 to 11.5% based on the total enteric granules, and the capsule in which the granules are filled is No. 1 or 2. Pharmacy Vol. 50(3) 230-238 (1990) reports that smaller capsules are more easily administered in view of an appearance organoleptic test, and a limit of a capsule size which can be easily administered is No. 3. Then, No. 1 or 2 capsule may reduce compliance of patients, in particular, elderly patients who have difficulty in swallowing.

OBJECTS OF THE INVENTION

In order to facilitate administration to patients, in particular, elderly or pediatric patients who have difficulty in swallowing, and to improve compliance, an object of the present invention is to produce stable enteric granules which comprises an acid-unstable medicament including a benzimidazole compound in a high content and a basic inorganic salt, and to render a size of a capsule in which the enteric granules are filled suitable for easy administration.

SUMMARY OF THE INVENTION

The present inventors have found that, in granules which contain an acid-unstable medicament, in particular, a benzimidazole compound and a basic inorganic salt as a stabilizing agent, and which are coated with an enteric layers or agents, the acid-unstable medicament can be stabilized even in high concentration and a high content, and can be easily administered to patients with improved compliance by adjusting a blending ratio of the basic inorganic salt to the acid-unstable medicament and an average particle size properly. The present inventors have further studied and, as a result, the present invention has been completed.

That is, the present invention provides:

(1) Granules comprising a principal ingredient layer containing an acid-unstable medicament in an amount of about 12% by weight or more based on the total granules; an intermediate coating layer which is formed on the principal ingredient layer; and an enteric coating layer which is formed on the intermediate coating layer; wherein said granules contain a basic inorganic salt, and have an average particle size of about 600 μm or more;

(2) The granules according to the above (1), wherein the basic inorganic salt is a magnesium salt or a calcium salt;

(3) The granules according to the above (1), wherein the acid-unstable medicament is a proton pump inhibitor (PPI);

(4) The granules according to the above (3), wherein the PPI is a benzimidazole compound represented by the formula (I):

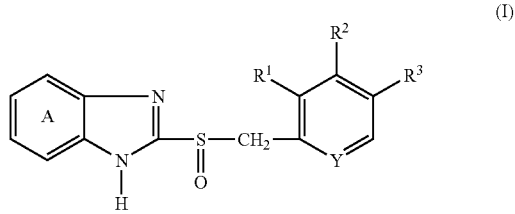

wherein ring A is an optionally substituted benzene ring, $R^1$, $R^2$ and $R^3$ are the same or different, and represent a hydrogen atom, an optionally substituted alkyl group, an optionally substituted alkoxy group, or an optionally substituted amino group, and Y represents a nitrogen atom or CH, or a salt thereof;

(5) The granules according to the above (3), wherein the PPI is lansoprazole, omeprazole, rabeprazole, pantoprazole, leminoprazole, tenatoprazole (TU-199), or an optically active isomer thereof, or a pharmaceutically acceptable salt thereof;

(6) The granules according to the above (3), wherein the PPI is lansoprazole, or an optically active isomer thereof, or a pharmaceutically acceptable salt thereof;

(7) The granules according to the above (4), wherein the basic inorganic salt is contained in the principal ingredient layer in an amount of about 0.2 part by weight to about 0.6 part by weight based on 1 part by weight of the benzimidazole compound;

(8) The granules according to the above (1) which are granules having a core, wherein the principal ingredient layer is formed on the core comprising at least one material selected from sucrose, starch, lactose and crystalline cellulose;

(9) The granules according to the above (1), wherein the enteric coating layer contains an enteric water-soluble polymer;

(10) The granules according to the above (9), wherein the enteric water-soluble polymer is a methacrylic acid copolymer;

(11) The granules according to the above (1), wherein an average particle size of the granules is about 1000 μm to about 2000 μm;

(12) The granules according to the above (4), wherein the benzimidazole compound is contained in an amount of about 12% by weight to about 40% by weight based on the total granules;

(13) A granular preparation, a capsule, a tablet, an effervescent preparation or a suspension comprising the granules according to the above (1);

(14) Granules comprising a principal ingredient layer containing a PPI in an amount of about 12% by weight to about 40% by weight based on the total granules, and one or more basic inorganic salts selected from the group consisting of basic salts of a sodium salt, a potassium salt, an aluminum salt, a magnesium salt and a calcium salt in an amount of about 0.2 part by weight to about 0.6 part by weight based on 1 part by weight of the PPI; an intermediate coating layer which is formed on the principal ingredient layer; and an enteric coating layer which is formed on the intermediate coating layer, and having an average particle size of about 1000 μm to about 2000 μm;

(15) A granular preparation, a capsule or a tablet comprising the granules according to the above (14);

(16) The preparation according to the above (15), which is a preparation for treating or preventing peptic ulcer, Zollinger-Ellison syndromes, gastritis, reflux esophagitis, symptomatic gastroesophageal reflux disease (symptomatic GERD), NUD (non ulcer dyspepsia), stomach cancer, gastric MALT lymphoma, ulcer resulting from nonsteroidal antiinflammatory medicaments, or excess stomach acid or ulcer due to post-operation stress, a preparation for eradicating *Helicobacter pylori*, or a preparation for suppressing upper gastrointestinal hemorrhage due to peptic ulcer, acute stress ulcer, hemorrhagic gastritis or invasion stress;

(17) Granules comprising a principal ingredient layer containing lansoprazole or an optically active isomer (R isomer) thereof in an amount of about 14% by weight to about 20% by weight based on the total granules, and one or more basic inorganic salts selected from the group consisting of basic salts of magnesium and calcium in an amount of about 0.2 part by weight to about 0.4 part by weight based on 1 part by weight of lansoprazole or an optically active isomer (R isomer) thereof; an intermediate coating layer which is formed on the principal ingredient layer; and an enteric coating layer which is formed on the intermediate coating layer, and having an average particle size of 1000 μm to about 2000 μm;

(18) The granules according to the above (17), wherein the basic inorganic salt is magnesium carbonate;

(19) No. 3 to 5 capsules comprising 30 mg of lansoprazole per one capsule;

(20) The capsule according to the above (19), wherein the granules according to the above (17) are filled;

(21) No. 4 to 5 capsules comprising 15 mg of lansoprazole per one capsule;

(22) The capsule according to the above (21), wherein the granules according to the above (17) are filled;

(23) No. 1 to 3 capsules comprising 60 mg of lansoprazole or an optically active isomer (R isomer) thereof per one capsule;

(24) The capsule according to the above (23), wherein the granule according to the above (17) is filled;

(25) No. 2 to 4 capsules comprising 40 mg of an optically active isomer (R isomer) of lansoprazole per one capsule;

(26) The capsule according to the above (25), wherein the granules according to the above (17) are filled;

(27) No. 3 to 5 capsules comprising 30 mg of an optically active isomer (R isomer) of lansoprazole per capsule;

(28) The capsule according to the above (27), wherein the granules as defined in the above (17) are filled; and

(29) A pharmaceutical composition which is a combination of an antimicrobial agent and the granules according to the above (3).

DETAILED DESCRIPTION OF THE INVENTION

The granules of the present invention are characterized in that they contain an acid-unstable medicament in high concentration, and have, at least, a principal ingredient layer, an intermediate coating layer which is formed on the principal ingredient layer, and further an enteric coating layer which is formed on the intermediate coating layer. The acid-unstable medicament as the principal active ingredient is contained in the principal ingredient layer but, structurally, the principal ingredient layer may have such a construction that it further has a core therein. And, the intermediate coating layer which is formed between the principal ingredient layer and the enteric coating layer has a stabilization function of the acid-unstable medicament contained in the principal ingredient layer by avoiding direct contact between the principal ingredient layer and the enteric coating layer.

The acid-unstable medicament in the present invention is not specifically limited, and may any medicaments which become unstable when exposed to an acid. Examples of such acid-unstable medicament include PPI having antiulcer activity, inter alia, benzimidazole compounds, imidazopyridine compounds, erythromycin antimicrobial compounds, and antiinflammatory enzymes such as serrapeptase, semialkaline proteinase, etc. and the like. In particular, the present invention is suitable for PPI such as benzimidazole compounds and imidazopyridine compounds having antiulcer activity. Hereinafter, the present invention will be illustrated with respect to benzimidazole compounds, but the present invention is not limited thereto, and can be similarly applied to other acid-unstable medicaments.

In the benzimidazole compounds having antiulcer activity used in the present invention, a preferred one is a compound of the above formula (I) in which ring A is a benzene ring which may be substituted with a halogen atom, an optionally halogenated $C_{1-4}$ alkyl group, an optionally halogenated $C_{1-4}$ alkoxy group and a 5- or 6-membered heterocyclic group, $R^1$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^2$ is a hydrogen atom, a $C_{1-6}$ alkoxy-$C_{1-6}$ alkoxy group or an optionally halogenated $C_{1-6}$ alkoxy group, $R^3$ is a hydrogen atom or a $C_{1-6}$ alkyl group, and Y is a nitrogen atom.

The particularly preferred one is a compound represented by the formula (Ia):

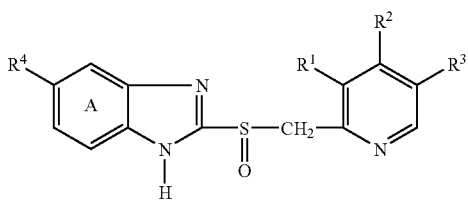

(Ia)

wherein $R^1$ represents a $C_{1-3}$ alkyl group or a $C_{1-3}$ alkoxy group, $R^2$ represents a $C_{1-3}$ alkoxy group which may be halogenated or substituted with a $C_{1-3}$ alkoxy group, $R^3$ represents a hydrogen atom or a $C_{1-3}$ alkyl group, and $R^4$ represents a hydrogen atom, an optionally halogenated $C_{1-3}$ alkoxy group or a pyrrolyl group (e.g. 1-, 2- or 3-pyrrolyl group).

In the above formula (Ia), the particularly preferred one is a compound in which $R^1$ is a $C_{1-3}$ alkyl group, $R^2$ is an optionally halogenated $C_{1-3}$ alkoxy group, $R^3$ is a hydrogen atom, and $R^4$ is a hydrogen atom or an optionally halogenated $C_{1-3}$ alkoxy group.

Examples of the "substituent" in the "optionally substituted benzene ring" represented by ring A in the compound represented by the above formula (I) [hereinafter, referred to as compound (I)] include a halogen atom, a cyano group, a nitro group, an optionally substituted alkyl group, a hydroxy group, an optionally substituted alkoxy group, an aryl group, an aryloxy group, a carboxy group, an acyl group, an acyloxy group, a 5- to 10-membered heterocyclic group, etc. and the benzene ring may be substituted with about one to three these substituents. When the number of substituents is 2 or more, respective substituents may be the same or different. Among these substituents, a halogen atom, an optionally substituted alkyl group, an optionally substituted alkoxy group, etc. is preferred.

Examples of the halogen atom include fluorine, chlorine and bromine atoms, etc. Inter alia, fluorine is preferred.

Examples of the "alkyl group" in the "optionally substituted alkyl group" include $C_{1-7}$ alkyl groups (e.g. methyl, ethyl, propyl, isopropyl, butyl, isobutyl, sec-butyl, tert-butyl, pentyl, hexyl, heptyl groups, etc.). As the "substituent" in the "optionally substituted alkyl group", there can be exemplified a halogen atom, a hydroxy group, $C_{1-6}$ alkoxy groups (e.g. methoxy, ethoxy, propoxy, butoxy, etc.), $C_{1-6}$ alkoxy-carbonyl groups (e.g. methoxycarbonyl, ethoxycarbonyl, propoxycarbonyl groups, etc.), a carbamoyl group, etc. and the number of these substituents may be about 1 to 3. When the number of substituents is 2 or more, respective substituents may be the same or different.

Examples of the "alkoxy group" in the "optionally substituted alkoxy group" include $C_{1-6}$ alkoxy groups (e.g. methoxy, ethoxy, propoxy, isopropoxy, butoxy, isobutoxy, pentoxy, etc.). Examples of the "substituent" in the "optionally substituted alkoxy group" include the same "substituents" as those for the above "substituent" in the "optionally substituted alkyl group", and the number of substituents is also the same as defined above.

Examples of the "aryl group" include $C_{6-14}$ aryl groups (e.g. phenyl, 1-naphthyl, 2-naphthyl, biphenyl, 2-anthryl groups, etc.) and the like.

Examples of the "aryloxy group" include $C_{6-14}$ aryloxy groups (e.g. phenyloxy, 1-naphthyloxy, 2-naphthyloxy groups, etc.) and the like.

Examples of the "acyl group" include formyl, alkylcarbonyl, alkoxycarbonyl, carbamoyl, alkylcarbamoly, alkylsulfinyl, alkylsulfonyl groups, and the like.

Examples of the "alkylcarbonyl group" include $C_{1-6}$ alkylcarbonyl groups (e.g. acetyl, propionyl groups, etc.) and the like.

Examples of the "alkoxycarbonyl group" include $C_{1-6}$ alkoxy-carbonyl groups (e.g. methoxycarbonyl, ethoxycarbonyl, propoxycarbonyl, butoxycarbonyl groups, etc.) and the like.

Examples of the "alkylcarbamoyl group" include N—$C_{1-6}$ alkyl-carbamoyl groups (e.g. methylcarbamoyl, ethylcarbamoyl groups, etc.), N,N-di-$C_{1-6}$ alkyl-carbamoyl groups (e.g. N,N-dimethycarbamoyl, N,N-diethylcarbamoyl groups, etc.) and the like.

Examples of the "alkylsulfinyl group" include $C_{1-7}$ alkylsulfinyl groups (e.g. methylsulfinyl, ethylsulfinyl, propylsulfinyl, isopropylsulfinyl groups, etc.).

Examples of the "alkylsulfonyl group" include $C_{1-7}$ alkylsulfonyl groups (e.g. methylsulfonyl, ethylsulfonyl, propylsulfonyl, isopropylsulfonyl groups, etc.).

Examples of the "acyloxy group" include an alkylcarbonyloxy group, an alkoxycarbonyloxy group, a carbamoyloxy group, an alkylcarbamoyloxy group, an alkylsulfinyloxy group, an alkylsulfonyloxy group and the like.

Examples of the "alkylcarbonyloxy group" include $C_{1-6}$ alkyl-carbonyloxy groups (e.g. acetyloxy, propionyloxy groups, etc.) and the like.

Examples of the "alkoxycarbonyloxy group" include $C_{1-6}$ alkoxy-carbonyloxy groups (e.g. methoxycarbonyloxy, ethoxycarbonyloxy, propoxycarbonyloxy, butoxycarbonyloxy groups, etc.) and the like.

Examples of the "alkylcarbamoyloxy group" include $C_{1-6}$ alkyl-carbamoyloxy groups (e.g. methylcarbamoyloxy, ethylcarbamoyloxy groups, etc.) and the like.

Examples of the "alkylsulfinyloxy group" include $C_{1-7}$ alkylsulfinyloxy groups (e.g. methylsulfinyloxy, ethylsulfinyloxy, propylsulfinyloxy, isopropylsulfinyloxy groups, etc.) and the like.

Examples of the "alkylsulfonyloxy group" include $C_{1-7}$ alkylsulfonyloxy groups (e.g. methylsulfonyloxy, ethylsulfonyloxy, propylsulfonyloxy, isopropylsulfonyloxy groups, etc.).

Examples of the "5- to 10-membered heterocyclic group" include 5- to 10-membered (preferably 5- or 6-membered) heterocyclic groups containing 1 or more (for example, 1 to 3) hetero atom(s) selected from a nitrogen atom, a sulfur atom and an oxygen atom in addition to carbon atoms, and specific examples thereof include a 2- or 3-thienyl group, a 2-, 3- or 4-pyridyl group, a 2- or 3-furyl group, a 1-, 2- or 3-pyrrolyl group, a 2-, 3-, 4-, 5- or 8-quinolyl group, a 1-, 3-, 4- or 5-isoquinolyl group, and a 1-, 2- or 3-indolyl group and the like. Among them, a preferred one is a 5- or 6-membered heterocyclic group such as a 1-, 2- or 3-pyrrolyl group, etc.

Preferably, ring A is a benzene ring optionally substituted with 1 or 2 substituent(s) selected from a halogen atom, an optionally halogenated $C_{1-4}$ alkyl group, an optionally halogenated $C_{1-4}$ alkoxy group and a 5- or 6-membered heterocyclic group.

Examples of the "optionally substituted alkyl group" represented by $R^1$, $R^2$ or $R^3$ include the above "optionally substituted alkyl group" described as the substituent for the above ring A.

Examples of the "optionally substituted alkoxy group" represented by $R^1$, $R^2$ or $R^3$ include the above "optionally substituted alkoxy group" described as the substituent for the above ring A.

Examples of the "optionally substituted amino group" represented by $R^1$, $R^2$ or $R^3$ include an amino group, mono-$C_{1-6}$ alkylamino groups (e.g. methylamino, ethylamino, etc.), mono-$C_{6-14}$ arylamino groups (e.g. phenylamino, 1-naphthylamino, 2-naphthylamino, etc.), di-$C_{1-6}$ alkylamino groups (e.g. dimethylamino, diethylamino, etc.), di-$C_{6-14}$ arylamino groups (e.g. diphenylamino, etc.) and the like.

Preferred $R^1$ is a $C_{1-6}$ alkyl group, a $C_{1-6}$ alkoxy group, a $C_{1-6}$ alkoxy-$C_{1-6}$ alkoxy group, or a di-$C_{1-6}$ alkylamino group. More preferred $R^2$ is a $C_{1-3}$ alkyl group or a $C_{1-3}$ alkoxy group.

Preferred $R^2$ is a hydrogen atom, a $C_{1-6}$ alkoxy-$C_{1-6}$ alkoxy group or an optionally halogenated $C_{1-6}$ alkoxy group. More preferred $R^3$ is a $C_{1-3}$ alkoxy group which is halogenated or optionally substituted with a $C_{1-3}$ alkoxy group.

Preferred $R^3$ is a hydrogen atom, or a $C_{1-6}$ alkyl group. More preferred $R^4$ is a hydrogen atom or a $C_{1-3}$ alkyl group (particularly a hydrogen atom).

Preferred Y is a nitrogen atom.

Specific examples of the compound (I) are the following compounds:
2-[[[3-methyl-4-(2,2,2-trifluoroethoxy)-2-pyridinyl]methyl]sulfinyl]-1H-imidazole (lansoprazole), 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl] sulfinyl]-1H-benzimidazole, etc.

Among these compounds, in particular, lansoprazole, that is, 2-[[[3-methyl-4-(2,2,2-trifluoroethoxy)-2-pyridinyl]methyl]sulfinyl]-1H-benzimidazole is preferred.

Examples of the imidazopyridine compound include tenatoprazole and the like.

The above compound (I) and imidazopyridine compound may be a racemic modification or optically active isomers such as R-isomer and S-isomer. For example, optically active isomers such as (R)-2-[[[3-methyl-4-(2,2,2-trifluoroethoxy)-2-pyridinyl]methyl]sulfinyl]-1H-benzimidazole (hereinafter, referred to as lansoprazole R isomer in some cases) and (S)-2-[[[3-methyl-4-(2,2,2-trifluoroethoxy)-2-pyridinyl]methyl]sulfinyl]-1H-benzimidazole (hereinafter, referred to as lansoprazole S isomer in some cases) are particularly suitable in the present invention. Usually, lansoprazole, lansoprazole R isomer, lansoprazole S isomer, etc. are preferably in the form of crystals. However, not only crystalline compounds but also amorphous compounds can be used because these compounds are stabilized by formulating into preparations and, additionally, these compounds are further stabilized by blending a basic inorganic salt therein and providing with an intermediate coating layer.

As a salt of the compound (I), a pharmaceutically acceptable salt is preferred, and examples thereof include a salt with an inorganic base, a salt with an organic base, a salt with a basic amino acid and the like.

Preferred examples of the salt with an inorganic base include alkali metal salts such as a sodium salt and a potassium salt; alkaline earth metal salts such as a calcium salt and a magnesium salt; an ammonium salt and the like.

Preferred examples of the salt with an organic base include salts with alkylamines (trimethylamine, triethylamine, etc.), heterocyclic amines (pyridine, picoline, etc.), alkanolamines (ethanolamine, diethanolamine, triethanolamine, etc.), dicyclohexylamine, N,N'-dibenzylethylenediamine and the like.

Preferred examples of the salt with a basic amino acid include salts with arginine, lysine, ornithine and the like.

Among these salts, an alkali metal salt or an alkaline earth metal salt is preferred. Inter alia, a sodium salt is preferred.

The compound (I) can be prepared by known per se methods, for example, the methods described in JP 61-50978 A, U.S. Pat. No. 4,628,098, JP 10-195068 A, WO 98/21201, JP 52-62275 A, JP 54-141783 A and the like, or similar methods. The optically active compound (I) can be obtained by an optical resolving method (fractionating recystallization method, chiral column method, diastereomer method, method using microorganisms or enzymes and the like), asymmetric oxidation method and the like. Lansoprazole R isomer can also be prepared by a process described, for example, in WO 00-78745, WO 01/83473 and the like.

As the benzimidazole compound having antiulcer activity used in the present invention, lansoprazole, omeprazole, rabeprazole, pantoprazole, leminoprazole, tenatoprazole (TU-199) and the like and optically active isomers thereof as well as pharmaceutically acceptable salts are preferred, and lansoprazole or an optically active isomer thereof, in particular, an R isomer is more preferred.

The amount of PPI to be formulated in the present invention varies depending on the kind of active component and dosage, and is for example, about 12% by weight to about 40% by weight, preferably about 12% by weight to about 20% by weight, more preferably about 14% by weight to about 20% by weight based on the total granules of the present invention. When PPI is the benzimidazole compound, in particular lansoprazole, the amount is about 14% by weight to about 20% by weight.

Examples of the basic inorganic salt used in the present invention include basic inorganic salts of sodium, potassium, magnesium and calcium. A preferred one is a basic inorganic salt of magnesium or calcium. A more preferred one is a basic inorganic salt of magnesium.

Examples of the basic inorganic salt of sodium include sodium carbonate, sodium bicarbonate, sodium hydroxide and the like.

Examples of the basic inorganic salt of potassium include potassium carbonate, potassium bicarbonate, potassium hydroxide and the like.

Examples of the basic inorganic salt of magnesium include ground magnesium carbonate, magnesium carbonate, magnesium oxide, magnesium hydroxide, magnesium aluminate metasilicate, magnesium silicate, magnesium aluminate, synthetic hydrotalcite [$Mg_6Al_2(OH)_{16}.CO_3.4H_2O$] and alumina magnesium hydroxide [$2.5MgO.Al_2O_3.xH_2O$], preferably, ground magnesium carbonate, magnesium carbonate, magnesium oxide, magnesium hydroxide and the like.

Examples of the basic inorganic salt of calcium include precipitated calcium carbonate, calcium hydroxide and the like.

More preferred examples of the basic inorganic salt include ground magnesium carbonate, magnesium carbonate, magnesium oxide, magnesium hydroxide and the like.

The basic inorganic salt used in the present invention may be a salt whose 1% aqueous solution or suspension has basic pH (pH 7 or higher).

The basic inorganic salt may be formulated alone or in combination of two or more thereof, and the amount to be formulated is about 0.2 to about 0.6 part by weight, preferably about 0.2 to about 0.4 part by weight based on 1 part by weight of PPI (benzimidazole compound, etc.). Inter alia, when PPI is lansoprazole or an optically active isomer thereof, preferably, the basic inorganic salt (preferably basic inorganic salt of magnesium or calcium, more preferably magnesium carbonate) is formulated in an amount of about 0.2 to about 0.4 part by weight based on 1 part by weight of PPI.

In the present invention, the "granules containing PPI (benzimidazole compound, etc.) in an amount of about 12% by weight to about 40% by weight based on the total granules, containing the basic inorganic salt as a stabilizing agent, and having an average particle size of about 600 μm or more" are preferred. When the particle size is smaller, it is difficult to increase concentration of the benzimidazole compound because a surface area becomes larger, which requires a larger amount of an enteric layer or agent. That is, in the present invention, it has been possible to decrease the amount of an enteric layer or agent by setting the particle size of at least about 600 μm or more, thereby increasing the concentration of the benzimidazole compound. The average particle size is about 600 to about 2500 μm. The more preferred average particle size is about 1000 to about 2000 μm. The granules may contain particles having a particle size of about 400 to about 3000 μm, preferably about 500 to about 2500 μm in so far as their average particle size, as a whole, is within the above range.

The particle size is measured by using a sieving method (Powder-Theory and Application-, p 475, 1979, Maruzen), and the average particle size is calculated based on an average of meshes of corresponding sieves and weight distribution. That is, arithmetic averaging is performed based on a product of an average and each weight.

The granules of the present invention can be prepared by a known granulation method. Examples of the granulation method include a rotary granulation method (e.g. centrifugal Fluid-bed granulation method), a fluidized granulation method, an agitation granulation method (e.g. agitator fluidized granulation method) and the like. Among them, a rotary granulation method and an agitation granulation method (agitator fluidized granulation method) are preferred.

Specific examples of the rotary granulation method include CF apparatus manufactured by Freund, etc. Specific examples of the agitator fluidized granulation method include methods using Spiral Flow manufactured by Freund, Multiplex manufactured by Powlex, New Malume manufactured by Fuji Powdal and the like. A method for spraying a binder solution can be appropriately selected according to the kind of a granulator and, for example, it may be any of a top spraying manner, a bottom spraying manner, a tangential spraying manner and the like.

Preferably, as described above, the granules of the present invention have a principal ingredient layer containing a principal ingredient, an intermediate coating layer which is formed on the principal ingredient layer, and an enteric coating layer which is formed on the intermediate coating layer.

For obtaining the granules having higher sphericity and narrower particle size distribution, in the present invention, the principal ingredient layer is formed by coating cores composed of one or more materials selected from sucrose, starch, lactose and microcrystalline cellulose with the benzimidazole compound. For example, granules having a core may be prepared by the method described in JP 63-301816 A. Such granules can be obtained by a method of coating a sugar core with a powdery spreading mixture containing the benzimidazole compound having antiulcer activity, the basic metal salt, an excipient, a disintegrating agent and the like, while spraying a binder solution of hydroxypropylcellulose on the sugar cores. Examples of the core granules include Nonpareil obtained by coating sucrose (75 parts by weight) with corn starch (25 parts by weight) by a known per se method, spherical core granules using microcrystalline cellulose, etc. Alternatively, core granules per se may be an active ingredient which becomes the above principal ingredient layer. An average particle size of the core granules is generally 14 to 80 mesh.

Examples of the cores include a spherical granulated material of sucrose and starch, a spherical granulated material of crystalline cellulose, a spherical granulated material of crystalline cellulose and lactose, etc.

It is desirable that cores are as uniformly spherical as possible so as to reduce variability of coating.

The proportion of the coating layer to the cores can be selected from within such a range that the dissolution property of the benzimidazole compound and a particle size of the granules can be controlled. For example, the proportion is usually about 0.2 part by weight to about 5 parts by weight, preferably about 0.1 part by weight to about 5 parts by weight based on 1 part by weight of the cores.

Coating layers with which the principal ingredient layer is coated may be formed of plural layers. The plural coating layers may contain various coating layers such as a coating layer for subcoating in addition to the intermediate coating layer containing no medicament and the enteric coating layer, and a particular combination of those coating layers may be appropriately selected.

In enteric coating granules containing an unstable principal ingredient such as the benzimidazole compound, etc., from a viewpoint of improvement in stability of the principal ingredient, it is preferable to arrange an intermediate coating layer between a principal ingredient layer containing the benzimidazole compound, etc. and an enteric coating layer to block direct contact between the layers because the enteric coating layer component is an acidic substance.

Such an intermediate coating layer may be a coating layer which can prevent contact between the benzimidazole compound as a basis and an enteric coating layer, and the amount and material of the coating layer are not limited in so far as such an objective is achieved. For example, there is a layer in which a saccharide such as sucrose [refined white sugar (pulverized (powdered sugar) or not pulverized), etc.], starch sugar such as corn starch, lactose, honey, sugar alcohol (D-mannitol, erythritol, etc.), etc. is appropriately formulated into a polymer base such as low-substituted hydroxypropylcellulose, hydroxypropylcellulose, hydroxypropylmethylcellulose (e.g. TC-5, etc.), polyvinylpyrrolidone, polyvinyl alcohol, methylcellulose, hydroxyethylmethylcellulose and the like. In addition, to the intermediate coating layer may be appropriately added an excipient (e.g. masking agent (titanium oxide, etc.), and an antistatic agent (titanium oxide, talc, etc.)) which are added for formulating into a preparation as needed, as described hereinafter.

The amount of the intermediate coating layer to be coated is usually about 0.02 part by weight to about 1.5 parts by weight, preferably about 0.05 part by weight to about 1 part by weight based on 1 part by weight of the granules containing, for example, benzimidazole. Coating can be performed according to a conventional method. For example, preferably, these intermediate coating layer components are diluted with purified water or the like to obtain a liquid, which is sprayed for coating. At this time, it is preferable to perform coating while spraying a binder agent of hydroxypropylcellulose or the like.

Examples of the "enteric coating layer" to be used for coating the granules in the present invention include aqueous enteric polymer bases such as cellulose acetate phthalate (CAP), hydroxypropylmethylcellulose phthalate, hydroxymethylcellulose acetate succinate, methacrylic acid copolymer, carboxymethylethylcellulose, shellac and the like, sustained-release bases such as ethyl acrylate-methacrylic acid copolymer and the like, and plasticizers such as water-soluble polymer, triethyl citrate, polyethylene glycol, acetylated monoglyceride, triacetin, castor oil and the like. They can be used alone or in combination of two or more thereof.

The enteric coating layer is an enteric polymer base, preferably an aqueous enteric methacrylic acid copolymer.

The amount of the enteric coating layer to be coated is about 10% by weight to about 70% by weight, preferably about 10% by weight to about 50% by weight, more preferably about 15% by weight to about 30% by weight based on the total amount of the granules before coating of the enteric coating.

Further, additives for formulating into pharmaceutical preparations can be used, and examples thereof include excipients (e.g. glucose, fructose, lactose, sucrose, D-mannitol, erythritol, maltitol, trehalose, sorbitol, corn starch, potato starch, wheat starch, rice starch, crystalline cellulose, anhydrous silicic acid, anhydrous calcium phosphate, precipitated calcium carbonate, calcium silicate, etc.), binders (e.g. hydroxypropylcellulose, hydroxypropylmethylcellulose, polyvinylpyrrolidone, methylcellulose, polyvinyl alcohol, sodium carboxymethylcellulose, partial α-starch, α-starch, sodium alginate, pullulan, gum arabic powder, gelatin etc.), disintegrating agents (e.g. low-substituted hydroxypropylcellulose, carmellose, potassium carmellose, sodium carboxymethylstarch, sodium crosscarmellose, crosspovidone, hydroxypropylstarch, etc.), corrigents (e.g. citric acid, ascorbic acid, tartaric acid, malic acid, aspartame, potassium acesulfame, sormatin, saccharin sodium, dipotassium glycyrrhizin, sodium glutamate, sodium 5'-inosinate, sodium 5'-guanylate, etc.), surfactants (e.g. polysorbates (polysorbate 80, etc.), polyoxyethylene-polyoxypropylene copolymer, sodium laurylsulfate, etc.), flavors (e.g. lemon oil, orange oil, menthol, mint oil, etc.), lubricants (e.g. magnesium stearate, sucrose fatty acid esters, sodium stearyl fumarate, stearic acid, talc, polyethylene glycol, etc.), colorants (e.g. titanium oxide, edible Yellow No. 5, edible Blue No. 2, iron sesquioxide, yellow iron sesquioxide etc.), antioxidants (e.g. sodium ascorbate, L-cysteine, sodium sulfite, etc.), masking agents (e.g. titanium oxide, etc.), antistatic agents (e.g. talc, titanium oxide, etc.) and the like.

The particle size of raw materials used for these materials is not particularly limited, but particles of about 500 μm or smaller are preferred from a viewpoint of manufacturing properties and administration properties.

The granules of the present invention can also be used in granular preparations, capsules, tablets, effervescent preparations, suspensions or the like.

From a viewpoint of easy handling, etc., capsules and tablets are preferred. As capsules, gelatin capsules, HPMC capsules, pullulan capsules and the like may be used. When used as capsules, capsules of No. 3 to No. 5 in size are preferable for easy administration. For example, in case of a capsule containing lansoprazole-containing granules, preferably, granules having an average particle size of about 1000 μm to about 2000 μm are prepared by providing an intermediate coating layer on a principal ingredient layer, which contains lansoprazole in an amount of about 14% by weight to about 20% by weight based on the total granules and a basic salt of magnesium and/or calcium in an amount of about 0.2 part by weight to about 0.4 part by weight based on 1 part by weight of lansoprazole, and then providing an enteric coating layer thereon, and the granules are filled in a capsule. As a capsule containing 30 mg of lansoprazole per capsule, conventional products are No. 1 to No. 2 capsules, while No. 3 to No. 5 stable capsules can be produced according to the present invention. In addition, in case of a capsule containing 15 mg of lansoprazole per capsule in which the above granules are filled, it is possible to reduce the size to No. 4 to No. 5 capsules. Further, in case of a capsule containing 60 mg of lansoprazole R isomer, No. 3 to No. 1 capsules are possible. Furthermore, in case of a capsule containing 40 mg, No. 4 to No. 2 capsules are possible and, in case of a capsule containing 30 mg, No. 5 to No. 3 capsules are possible.

In the granules of the present invention, since PPI such as the benzimidazole compound has excellent antiulcer activity, gastric acid secretion inhibiting activity, mucosa protecting activity, anti-*Helicobacter pylori* activity and the like, and has low toxicity, they are useful for medicine. In this case, the granules of the present invention can be administered to a mammal (e.g. human, monkey, sheep, horse, dog, cat, rabbit, rat, mouse, etc.) orally for the purpose of treating and preventing peptic ulcers (e.g. gastric ulcer, duodenal ulcer, stomal ulcer, etc.), Zollinger-Ellison syndromes, gastritis, reflux esophagitis, symptomatic gastroesophageal reflux disease (symptomatic GERD)), NUD (non ulcer dyspepsia), stomach cancer (including stomach cancer accompanied with promotion of production of interleukin-1β due to genetic polymorphism of interleukin-1), gastric MALT lymphoma and the like, eradicating *Helicobacter pylori*, suppressing upper gastrointestinal hemorrhage due to peptic ulcers, acute stress ulcer and hemorrhagic gastritis, suppressing upper digestive tract hemorrhagic due to invasion stress (stress resulting from major operation requiring post-operative intensive management, and cerebrovascular disorder, head trauma, multiple organ failure and diffuse burn requiring intensive care), treating and preventing ulcers resulting from nonsteroidal antiinflammatory medicaments; treating and preventing excess stomach acid and ulcer due to post-operation stress, and the like. For eradicating *Helicobacter pylori*, etc., the granules or capsule of the present invention may be used together with other active component(s) (e.g. 1 to 3 active component(s)).

Examples of the "other active component(s)" include anti-*Helicobacter pylori* active substances, antimicrobial agents such as imidazole compounds, quinolone compounds, and bismuth salts. Inter alia, medicines comprising a combination of the granules or capsule of the present invention and an antimicrobial agent are preferred. Among them, a combination with anti-*Helicobacter pylori* active substances, or antimicrobial agents such as imidazole compounds is preferred. Examples of the "anti-*Helicobacter pylori* active substance" include penicillin antibiotics (e.g. amoxicillin, benzylpenicillin, piperacillin, mecillinam, etc.), cephem antibiotics (e.g. cefixime, cefaclor, etc.), macrolide antibiotics (e.g. erythromycin antibiotics such as erythromycin, clarithromycin, etc.), tetracycline antibiotics (e.g. tetracycline, minocycline, streptomycin, etc.), aminoglycoside antibiotics (e.g. gentamycin, amikacin, etc.), imipenem and the like. Inter alia, penicillin antibiotics and macrolide antibiotics are preferred.

Examples of the "imidazole compound" include metronidazole, miconazole, etc. Examples of the "bismuth salt" include bismuth acetate, bismuth citrate, etc. Antibacterial agents of "quinolone compounds" are also preferred, and examples thereof include ofloxacin, ciprofloxacin, etc. Inter alia, for eradicating *Helicobacter pylori*, it is preferred to use the granules or capsule of the present invention in combination with penicillin antibiotics (e.g. amoxicillin, etc.) and/or erythromycin antibiotics (e.g. clarithromycin etc.).

For example, in case of lansoprazole, in many cases, a conventional 15 mg-containing capsule is a product filled in a No. 3 capsule, and a conventional 30 mg-containing capsule is a product filled in a No. 1 capsule. However, according to the present invention, since the amounts of components other than a basis can be reduced without deteriorating stability of the basis and a preparation, the size of a 15 mg-containing capsule can be reduced to No. 4 to No. 5 capsules, and the size of a 30 mg-containing capsule can be reduced to No. 3 to No. 5 capsules, respectively.

Further, even in a 60 mg-containing capsule, it is possible to use No. 1 to No. 3 capsules.

Furthermore, in case of an optically active isomer of lansoprazole, No. 3 to No. 5 capsules, No. 2 to No. 4 capsules and No. 1 to No. 3 capsules can be used for 30 mg-, 40 mg- and 60 mg-containing capsules, respectively.

For example, because of a high content of an active component and easy administration, a capsule containing 60 mg of lansoprazole or lansoprazole R isomer is suitable for treating, inter alia, acid hypersecretion symptom including Zollinger-Ellison syndromes.

A daily dosage varies depending on the degree of symptom, the age, sex and weight of subject, the administration time, interval, and the kind of principal or active ingredient, etc., and is not specifically limited. For example, when orally administered to an adult (60 kg) as an antiulcer agent, a dosage is about 0.5 to 1500 mg/day, preferably about 5 to 150 mg/day in terms of an active component. These benzimidazole compound-containing preparations may be administered once or by dividing into 2 to 3 times daily.

Hereinafter, the present invention will be illustrated in more detail by Examples, but the present invention is not limited by them. In the following Examples, lansoprazole and its optically active isomer in the form of crystals were used.

EXAMPLE 1

Lansoprazole, magnesium carbonate, sucrose (pulverized sucrose), corn starch and low-substituted hydroxypropylcellulose were thoroughly mixed to obtain a spreading mixture of principal ingredient. Spherical granules consisting of sucrose and starch were placed in an agitator fluidized granulation coating machine (MP-10 manufactured by Powlex), and the above spreading mixture of principal ingredient was coated while spraying a hydroxypropylcellulose solution (2.5%: W/W) to obtain spherical granules. The resultant spherical granules were dried in a vacuum at 40° C. for 16 hours, and passed through a round sieve to obtain granules of 500 μm to 1180 μm.

| Granules Composition in 150 mg | |
| --- | --- |
| Spherical granules consisting of sucrose and starch | 50 mg |
| Lansoprazole | 30 mg |
| Magnesium carbonate | 10 mg |
| Sucrose (pulverized sucrose) | 30 mg |
| Corn starch | 14 mg |
| Low-substituted hydroxypropylcellulose | 15 mg |
| Hydroxypropylcellulose | 1 mg |
| Purified water | 39 μl |
| Total | 150 mg |

An enteric suspension having the following composition was coated on the above granules using an agitator fluidized granulation coating machine (MP-10, manufactured by Powlex), which were dried as such, and passed through a round sieve to obtain enteric granules of 710 to 1420 μm. Into the resultant granules were mixed talc and aerosil, and 190 mg of the resultant mixed granules were filled into a No. 3 capsule manually.

| Composition of enteric suspension | |
| --- | --- |
| Methacrylic acid copolymer | 86.7 mg (solid components 26 mg) |
| Talc | 7.8 mg |
| Polyethylene glycol | 2.5 mg |
| Titanium oxide | 2.5 mg |
| Polysorbate 80 | 1.0 mg |
| Purified water | 119.5 μl |
| Total | 39.8 mg (as solids) |
| Composition of enteric granules | |
| Granules | 150 mg |
| Enteric coating layer | 39.8 mg |
| Total | 189.8 mg |
| Composition of mixed granules | |
| Enteric granules | 189.8 mg |
| Talc | 0.1 mg |
| Aerosil | 0.1 mg |
| Total | 190 mg |
| Composition of capsule | |
| Mixed granules | 190 mg |
| No. 3 capsule | 1 |

In addition, particle size distribution of the resultant mixed granules was measured using a round sieve, and the results are shown below:

| | |
| --- | --- |
| 1180 μm remaining | 10.6% |
| 1180/1000 μm | 70.9% |
| 1000/850 μm | 12.0% |
| 850 μm pass | 6.4% |

EXAMPLE 2

Lansoprazole, magnesium carbonate, sucrose (pulverized sucrose), corn starch and low-substituted hydroxypropylcellulose were thoroughly mixed to obtain a spreading mixture of principle ingredient. Sucrose (pulverized sucrose), corn starch and low-substituted hydroxypropylcellulose were thoroughly mixed to obtain a spreading mixture for intermediate layer. Spherical granules consisting of sucrose and starch were placed in a centrifugal Fluid-bed granulator (CF-360φ manufactured by Freund), and the above spreading mixture of principal ingredient and the spreading mixture for intermediate layer were coated while spraying a hydroxypropylcellulose solution (2.5%: W/W) to obtain spherical granules. The resultant spherical granules were dried in a vacuum at 40° C. for 16 hours, and passed through a round sieve to obtain granules of 500 μm to 1180 μm.

| Granules Composition in 160 mg | |
| --- | --- |
| Spherical granules consisting of sucrose and starch | 50 mg |
| Spreading mixture of principal ingredient | |
| Lansoprazole | 30 mg |
| Magnesium carbonate | 10 mg |
| Sucrose (pulverized sucrose) | 30 mg |
| Corn starch | 14 mg |

| Granules Composition in 160 mg | |
|---|---|
| Low-substituted hydroxypropylcellulose | 15 mg |
| Spreading mixture for intermediate layer | |
| Sucrose (pulverized sucrose) | 5 mg |
| Corn starch | 2.5 mg |
| Low-substituted hydroxypropylcellulose | 2.5 mg |
| Binder solution | |
| Hydroxypropylcellulose | 1 mg |
| Purified water | 34 μl |
| Total | 160 mg |

An enteric suspension having the following composition was coated on the above granules using an agitator fluidized granulation coating machine (MP-10 manufactured by Powlex), which was dried as such, and passed through a round sieve to obtain enteric granules of 600 to 1420 μm. Into the resultant granules were mixed talc and aerosil, and 200 mg of the resultant mixed granules were filled into a No. 3 capsule.

| Composition of enteric suspension | |
|---|---|
| Methacrylic acid copolymer | 86.7 mg (solid components 26 mg) |
| Talc | 7.8 mg |
| Polyethylene glycol | 2.5 mg |
| Titanium oxide | 2.5 mg |
| Polysorbate 80 | 1.0 mg |
| Purified water | 119.5 μl |
| Total | 39.8 mg (as solids) |
| Composition of enteric granules | |
| Granules | 160 mg |
| Enteric coating layer | 39.8 mg |
| Total | 199.8 mg |
| Composition of mixed granules | |
| Enteric granules | 199.8 mg |
| Talc | 0.1 mg |
| Aerosil | 0.1 mg |
| Total | 200 mg |
| Composition of capsule | |
| Mixed granules | 200 mg |
| No. 3 capsule | 1 |

In addition, particle size distribution of the resultant mixed granules was measured using a round sieve, and the results are shown below:

| | |
|---|---|
| 1180 μm remaining | 20.2% |
| 1180/1000 μm | 76.2% |
| 1000/850 μm | 3.6% |
| 850/710 μm | 0.0% |
| 710 μm passed | 0.0% |

EXAMPLE 3

A suspension was prepared by using lansoprazole, magnesium carbonate, low-substituted hydroxypropylcellulose, hydroxypropylcellulose and purified water. Microcrystalline cellulose spherical granules were placed in an agitator fluidized granulation coating machine (MP-10 manufactured by Powlex), and the suspension was coated while spraying the suspension to obtain spherical granules. The granules were dried as such, and passed through a round sieve to obtain granules of 500 μm to 1180 μm.

| Granules Composition in 70 mg | |
|---|---|
| Microcrystalline cellulose spherical granules | 20 mg |
| Lansoprazole | 30 mg |
| Magnesium carbonate | 10 mg |
| Low-substituted hydroxypropylcellulose | 5 mg |
| Hydroxypropylcellulose | 5 mg |
| Purified water | 100 μl |
| Total | 70 mg |

An intermediate layer suspension was prepared by using hydroxypropylmethylcellulose, low-substituted hydroxypropylcellulose, D-mannitol and purified water. The granules containing lansoprazole were placed in an agitator fluidized granulation coating machine (MP-10 manufactured by Powlex), and an intermediate layer was coated while spraying the suspension to obtain spherical granules. The granules were dried as such and passed through a round sieve to obtain granules of 500 μm to 1800 μm.

| Granules Composition in 80 mg | |
|---|---|
| Lansoprazole-containing granules | 70 mg |
| Hydroxypropylmethylcellulose | 5 mg |
| Low-substituted hydroxypropylcellulose | 2.5 mg |
| D-mannitol | 2.5 mg |
| Purified water | 40 μl |
| Total | 80 mg |

An enteric suspension having the following composition was coated on the above granules using an agitator fluidized granulation coating machine (MP-10 manufactured by Powlex), which was dried as such, and passed through a round sieve to obtain enteric granules of 600 to 1420 μm. Into the resultant granules were mixed talc and aerosil, and 100 mg of the resultant mixed granules were filled in a No. 5 capsule.

| Composition of enteric suspension | |
|---|---|
| Methacrylic acid copolymer | 43.3 mg (solid components 13 mg) |
| Talc | 3.8 mg |
| Polyethylene glycol | 1.2 mg |
| Titanium oxide | 1.2 mg |
| Polysorbate 80 | 0.5 mg |
| Purified water | 60 μl |
| Total | 19.7 mg (as solids) |
| Composition of enteric granules | |
| Granules | 80 mg |
| Enteric coating layer | 19.7 mg |
| Total | 99.7 mg |

-continued

| Composition of mixed granules | |
|---|---|
| Enteric granules | 99.7 mg |
| Talc | 0.2 mg |
| Aerosil | 0.1 mg |
| Total | 100 mg |
| Composition of capsule | |
| Mixed granules | 100 mg |
| No. 5 capsule | 1 |

In addition, particle size distribution of the resultant mixed granules was measured using a round sieve, and the results are shown below:

| | |
|---|---|
| 1180 μm remaining | 5.6% |
| 1180/1000 μm | 91.3% |
| 1000/850 μm | 3.1% |
| 850 μm passed | 0.0% |

EXAMPLE 4

Lansoprazole, magnesium carbonate, sucrose (pulverized sucrose), corn starch, low-substituted hydroxypropylcellulose and hydroxypropylcellulose were thoroughly mixed to obtain a spreading mixture of principal ingredient. Sucrose (pulverized sucrose), corn starch, low-substituted hydroxypropylcellulose and hydroxypropylcellulose were thoroughly mixed to obtain a spreading mixture for intermediate layer. Spherical granules consisting of sucrose and starch were placed in a centrifugal Fluid-bed granulator (CF-1300φ manufactured by Freund) and the above spreading mixture of principal ingredient and the spreading mixture for intermediate layer were coated while spraying purified water to obtain spherical granules. The resultant spherical granules were dried in a vacuum at 45° C. for 18 hours, and passed through a vibrating screen to obtain granules of 500 μm to 1180 μm.

| Granules Composition in 320 mg | |
|---|---|
| Spherical granules consisting of sucrose and starch | 100 mg |
| Spreading mixture of principal ingredient | |
| Lansoprazole | 60 mg |
| Magnesium carbonate | 20 mg |
| Sucrose (pulverized sucrose) | 60 mg |
| Corn starch | 28 mg |
| Low-substituted hydroxypropylcellulose | 30 mg |
| Hydroxypropylcellulose | 1.8 mg |
| Spreading mixture for intermediate layer | |
| Sucrose (pulverized sucrose) | 10 mg |
| Hydroxypropylcellulose | 0.2 mg |
| Purified water | 60 μl |
| Total | 320 mg |

An enteric suspension having the following composition was coated on the above granules using a fluidized bed coating machine (FLO-90 manufactured by Freund), which was dried as such, and passed through a vibrating screen to obtain enteric granules of 600 to 1420 μm. To the resultant granule were mixed talc and aerosil using a tumbler mixer (manufactured by Showa Kagakukikai-kousakusho, 1300 L), and 400 mg of the resultant mixed granules were filled in a No. 1 capsule using a capsule filler (MATIC-90 manufactured by IMA).

| Composition of enteric suspension | |
|---|---|
| Methacrylic acid copolymer | 173.4 mg (solid components 52 mg) |
| Talc | 15.6 mg |
| Polyethylene glycol | 5.0 mg |
| Titanium oxide | 5.0 mg |
| Polysorbate 80 | 2.0 mg |
| Purified water | 239 μl |
| Total | 79.6 mg (as solids) |
| Composition of enteric granules | |
| Granules | 320 mg |
| Enteric coating layer | 79.6 mg |
| Total | 399.6 mg |
| Composition of mixed granules | |
| Enteric granules | 399.6 mg |
| Talc | 0.2 mg |
| Aerosil | 0.2 mg |
| Total | 400 mg |
| Composition of capsule | |
| Mixed granules | 400 mg |
| No. 1 capsule | 1 |

In addition, particle size distribution of the resultant mixed granules was measured using a round sieve, and the results are shown below:

| | |
|---|---|
| 1180 μm remaining | 2.6% |
| 1180/1000 μm | 92.2% |
| 1000/850 μm | 4.6% |
| 850/710 μm | 0.4% |
| 710 μm passed | 0.2% |

EXAMPLE 5

A composition is shown in Table 1. Lansoprazole R isomer, magnesium carbonate, sucrose (pulverized sucrose), corn starch and low-substituted hydroxypropylcellulose were thoroughly mixed to obtain a spreading mixture of principal ingredient. In addition, sucrose (pulverized sucrose), corn starch and low-substituted hydroxypropylcellulose were thoroughly mixed to obtain a spreading mixture of intermediate layer. Spherical granulates consisting of sucrose and starch were placed in a centrifugal Fluid-bed granulator (CF manufactured by Freund), and the above spreading mixture of principal ingredient and the spreading mixture for intermediate layer were successively coated while spraying a hydroxypropylcellulose solution (2%: W/W) to obtain spherical granules. The coating operation conditions were as follows: rotor rotating speed: 300 rpm, spray rate: 1.8 g/min, spray air pressure: 0.2 kg/cm², and slit air pressure: 0.2 kg/cm². The resultant spherical granules were dried in a vacuum at 40° C. for 20 hours and passed through a round sieve to obtain granules of 710 μm to 1420 μm.

An enteric suspension was coated on the above granules using a fluidized granulation coating machine (LAB-1 manufactured by Powlex), which was dried as such, and passed through a round sieve to obtain enteric granules of 850 to 1420 μm. The coating operation conditions were as follows:

inlet air volume: 0.6 m³/min, inlet air temperature: 85° C., spray rate: 8 g/min, and spray air pressure: 1 kg/cm².

Into the resultant granules were mixed talc and aerosil, and 150 mg (corresponding to 30 mg of lansoprazole R isomer), 200 mg (corresponding to 40 mg of lansoprazole R isomer) and 300 mg (corresponding to 60 mg of lansoprazole R isomer) of the resultant mixed granules were filled in No. 4, No. 3 and No. 2 capsules, respectively.

EXAMPLE 6

A composition is shown in Table 1. Lansoprazole R isomer, magnesium carbonate, sucrose (pulverized sucrose) and low-substituted hydroxypropylcellulose were thoroughly mixed to obtain a spreading mixture of principal ingredient. In addition, sucrose (pulverized sucrose), low-substituted hydroxypropylcellulose and titanium oxide were thoroughly mixed to obtain a spreading mixture for intermediate layer. Spherical granules consisting of sucrose and starch were placed in a centrifugal Fluid-bed granulator (CF manufactured by Freund), the above spreading mixture of principal ingredient and the spreading mixture for intermediate layer were successively coated while spraying a hydroxypropylcellulose solution (2%: W/W) to obtain spherical granules. The coating operation conditions were as follows: rotor rotating speed: 300 rpm, spray rate: 1.8 g/min, spray air pressure: 0.2 kg/cm², and slit air pressure: 0.2 kg/cm². The resultant spherical granules were dried in a vacuum at 40° C. for 20 hours, and passed through a round sieve to obtain granules of 710 μm to 1420 μm.

An enteric suspension was coated on the above granules using a fluidized granulation coating machine (LAB-1 manufactured by Powlex), which was dried as such, and passed through a round sieve to obtain enteric granules of 850 to 1420 μm. The coating operation conditions were as follows: inlet air volume: 0.6 m³/min, inlet air temperature: 85° C., spray rate: 8 g/min, and spray air pressure: 1 kg/cm².

Into the resultant granules were mixed talc and aerosil, and 150 mg (corresponding to 30 mg of lansoprazole R isomer), 200 mg (corresponding to 40 mg of lansoprazole R isomer) and 300 mg (corresponding to 60 mg of lansoprazole R isomer) of the resultant mixed granules were filled in No. 4, No. 3 and No. 2 capsules, respectively.

EXAMPLE 7

A composition is shown in Table 1. Lansoprazole R isomer, magnesium carbonate, sucrose (pulverized sucrose), low-substituted hydroxypropylcellulose and titanium oxide were thoroughly mixed to obtain a spreading mixture of principal ingredient. Spherical granules consisting of sucrose and starch were placed in a centrifugal Fluid-bed granulator (CF manufactured by Freund), and the above spreading mixture of principal ingredient was coated while spraying a hydroxypropylcellulose solution (2%: W/W) to obtain spherical granules. The coating operation conditions were as follows: rotor rotating speed: 300 rpm, spray rate: 1.8 g/min, spray air pressure: 0.2 kg/cm², and slit air pressure: 0.2 kg/cm². The resultant spherical granules were dried in a vacuum at 40° C. for 20 hours, and passed through a round sieve to obtain granules of 710 μm to 1420 μm.

An enteric suspension was coated on the above granules using a fluidized granulation coating machine (LAB-1 manufactured by Powlex), which was dried as such, and passed though a round sieve to obtain enteric granules of 850 to 1420 μm. The coating operation conditions were as follows: inlet air volume: 0.6 m³/min, inlet air temperature: 85° C., spray rate: 8 g/min, and spray air pressure: 1 kg/cm².

Into the resultant granules were mixed talc and aerosil, and 150 mg (corresponding to 30 mg of lansoprazole R isomer), 200 mg (corresponding to 40 mg of lansoprazole R isomer) and 300 mg (corresponding to 60 mg of lansoprazole R isomer) of the resultant mixed granules were filled in No. 4, No. 3 and No. 2 capsules, respectively.

TABLE 1

Composition table

Granules Composition in 160 mg

|  | Example 5 | Example 6 | Example 7 |
|---|---|---|---|
| Spherical granules consisting of sucrose and starch | 50 mg | 50 mg | 50 mg |
| Spreading mixture of principal ingredient |  |  |  |
| Lansoprazole R isomer | 40 mg | 40 mg | 40 mg |
| Magnesium carbonate | 14 mg | 14 mg | 14 mg |
| Sucrose (pulverized sucrose) | 26 mg | 26 mg | 36 mg |
| Corn starch | 9 mg | 0 mg | 0 mg |
| Low-substituted hydroxypropylcellulose | 10 mg | 10 mg | 12.5 mg |
| Titanium oxide | 0 mg | 0 mg | 6.5 mg |
| Spreading mixture for intermediate layer |  |  |  |
| Sucrose (pulverized sucrose) | 5 mg | 10 mg |  |
| Corn starch | 2.5 mg | 0 mg |  |
| Low-substituted hydroxypropylcellulose | 2.5 mg | 2.5 mg |  |
| Titanium oxide | 0 mg | 6.5 mg |  |
| Binder solution |  |  |  |
| Hydroxypropylcellulose | 1 mg | 1 mg | 1 mg |
| Purified water | 49 μl | 49 μl | 49 μl |
| Total | 160 mg |  |  |

Composition of enteric suspension

| Methacrylic acid copolymer | 86.7 mg (solid components 26 mg) |
|---|---|
| Talc | 7.8 mg |
| Polyethylene glycol | 2.5 mg |
| Titanium oxide | 2.5 mg |
| Polysorbate 80 | 1.0 mg |
| Purified water | 119.5 μl |
| Total | 39.8 mg (as solids) |

Composition of enteric granules

| Granules | 160 mg |
|---|---|
| Enteric coating layer | 39.8 mg |
| Total | 199.8 mg |

Composition of mixed granules

| Enteric granules | 199.8 mg |
|---|---|
| Talc | 0.1 mg |
| Aerosil | 0.1 mg |
| Total | 200 mg |

Composition of capsules

| Lansoprazole R isomer | corresponding to 30 mg | corresponding to 40 mg | corresponding to 60 mg |
|---|---|---|---|
| Mixed granules | 150 mg | 200 mg | 300 mg |
| Capsule | 1 (No. 4) | 1 (No. 3) | 1 (No. 2) |

EXAMPLE 8

A composition is shown in Table 2. Lansoprazole R isomer, magnesium carbonate, sucrose (pulverized sucrose), corn starch and low-substituted hydroxypropylcellulose were thoroughly mixed to obtain a spreading mixture of principal ingredient. Spherical granules consisting of sucrose and starch were placed in a centrifugal Fluid-bed granulator (CF manufactured by Freund), and the above spreading mixture of principal ingredient was successively coated while spraying a hydroxypropylcellulose solution (2%: W/W) to obtain spherical granules. The coating operation conditions were as follows: rotor rotating speed: 300 rpm, spray rate: 1.8 g/min, spray air pressure: 0.2 kg/cm², and slit air pressure: 0.2 kg/cm². The resultant spherical granules were dried in a vacuum at 40° C. for 20 hours, and passed through a round sieve to obtain granules of 710 μm to 1420 μm.

A suspension composed of hydroxypropylmethylcellulose, titanium oxide and purified water shown in Table 2 was prepared. This suspension was coated on the above granules using a fluidized granulation coating machine (LAB-1 manufactured by Powlex), which was dried as such, and passed through a round sieve to obtain enteric granules of 850 to 1420 μm. The coating operation conditions were as follows: inlet air rate: 0.8 to 1 m³/min, inlet air temperature: 85° C., spray rate: 6 g/min, and spray air pressure: 0.8 to 1 kg/cm².

An enteric suspension was coated on the above granules using a fluidized granulation coating machine (LAB-1 manufactured by Powlex), which was dried as such, and passed through a round sieve to obtain enteric granules of 850 to 1420 μm. The coating operation conditions were as follows: inlet air rate: 0.6 m³/min, inlet air temperature: 85° C., spray rate: 8 g/min, and spray air pressure: 1 kg/cm².

Into the resultant granules were mixed talc and aerosil, and 150 mg (corresponding to 30 mg of lansoprazole R isomer), 200 mg (corresponding to 40 mg of lansoprazole R isomer) and 300 mg (corresponding to 60 mg of lansoprazole R isomer) of the resultant mixed granules were filled into No. 4, No. 3 and No. 2 capsules, respectively.

TABLE 2

Composition table

| Granules Composition in 141 mg | |
|---|---|
| Spherical granules consisting of sucrose and starch | 50 mg |
| Spreading mixture of principal ingredient | |
| Lansoprazole R isomer | 40 mg |
| Magnesium carbonate | 14 mg |
| Sucrose (pulverized sucrose) | 26 mg |
| Low-substituted hydroxypropylcellulose | 10 mg |
| Binder solution | |
| Hydroxypropylcellulose | 1 mg |
| Purified water | 49 μl |
| Total | 141 mg |
| Composition of intermediate layer suspension | |
| Hydroxypropylmethylcellulose | 12.5 mg |
| Titanium oxide | 6.5 mg |
| Purified water | 171 μl |
| Total | 19 mg (as solids) |
| Composition of intermediate layer coated granules | |
| Granules | 141 mg |
| Intermediate layer coating | 19 mg |
| Total | 160 mg |
| Composition of enteric suspension | |
| Methacrylic acid copolymer | 86.7 mg (solid components 26 mg) |
| Talc | 7.8 mg |
| Polyethylene glycol | 2.5 mg |
| Titanium oxide | 2.5 mg |
| Polysorbate 80 | 1.0 mg |
| Purified water | 119.5 μl |
| Total | 39.8 mg (as solids) |
| Composition of enteric granules | |
| Granules | 160 mg |
| Enteric coating layer | 39.8 mg |
| Total | 199.8 mg |
| Composition of mixed granules | |
| Enteric granules | 199.8 mg |
| Talc | 0.1 mg |
| Aerosil | 0.1 mg |
| Total | 200 mg |

Composition of capsules

| | | | |
|---|---|---|---|
| Lansoprazole R isomer | 30 mg equivalent | 40 mg equivalent | 60 mg equivalent |
| Mixed granules | 150 mg | 200 mg | 300 mg |
| Capsule | 1 (No. 4) | 1 (No. 3) | 1 (No. 2) |

Experiment 1

Each of the enteric granules (mixed granules) prepared in Examples 1 and 2 was stored in a tightly sealed bottle under 40° C./75% RH for 24 weeks and, thereafter, a content (remaining rate) and appearance change (ΔE) were measured. The content was measured by HPLC method. Appearance change (ΔE) was obtained by measuring a color difference (ΔE) using SM color computer SM-5 (manufactured by Suga Shikenki). The results are shown in Table 3.

TABLE 3

| | Example 1 | | Example 2 | |
|---|---|---|---|---|
| Storing conditions | ΔE | Content (remaining rate) | ΔE | Content (remaining rate) |
| Initial | — | 100% | — | 100% |
| 40° C. 75% RH tightly sealed 4 W | 1.73 | 100.0% | 2.84 | 99.7% |
| 40° C. 75% RH tightly sealed 12 W | 7.27 | 100.0% | 3.79 | 99.9% |
| 40° C. 75% RH tightly sealed 24 W | 3.88 | 98.7% | 5.06 | 100.4% |

As a result, it was revealed that the granules of the present invention had less appearance change and stable content.

Experiment 2

Each of the enteric granules (mixed granules) prepared in Examples 5 to 8 was stored in a tightly sealed glass bottle at 60° C. for 2 weeks and, thereafter, a content (remaining rate) was measured. The content was measured by HPLC method.

The results are shown in Table 4. Appearance change of the preparations of Examples 7 and 8 was hardly observed with naked eyes.

TABLE 4

Results of stability test of Examples 5 to 8
Storing conditions: 60° C. tightly sealed glass bottle, 2 weeks storage

| Example | Content (remaining rate) |
|---|---|
| Example 5 | 97.8% |
| Example 6 | 97.1% |
| Example 7 | 95.9% |
| Example 8 | 99.1% |

As a result, it was revealed that the granules of the present invention are stable from a viewpoint of the content.

INDUSTRIAL APPLICABILITY

By optimizing a blending ratio of a basic inorganic salt with an acid-unstable medicament, in particular, a benzimidazole compound, and an average particle size, unexpectedly, the granules of the present invention enabled the acid-unstable medicament to be stable even at high concentration and high content. In addition, since the granules of the present invention contains an active ingredient at high concentration, the amount of a whole preparation can be reduced even at the same content and, therefore, the size of a capsule or the like can be reduced, and a preparation which can be easily administered can be obtained. As a result, the preparation can be easily administered to patients, in particular, elderly and pediatric patients who have difficulty in swallowing, and compliance can be improved.

The invention claimed is:

1. A capsule comprising lansoprazole-containing granules, wherein said granules comprise:
a principal ingredient layer comprising lansoprazole or an optically active isomer thereof or a pharmaceutically acceptable salt thereof in an amount of 12% by weight or more based on the total granules, and one or more basic inorganic salts in an amount of 0.2 part by weight to 0.4 part by weight based on 1 part by weight of lansoprazole or the optically active isomer thereof or the pharmaceutically acceptable salt thereof;
an intermediate coating layer which is formed on the principal ingredient layer;
an enteric coating layer which is formed on the intermediate coating layer; and
a core;
wherein:
the principal ingredient layer is formed on the core,
the amount of the intermediate coating layer to be coated is 0.02 part by weight to 1.5 parts by weight on 1 part by weight of the granules containing lansoprazole or the optically active isomer thereof or the pharmaceutically acceptable salt thereof,
the amount of the enteric coating layer to be coated is 10% by weight to 70% by weight based on the total amount of the granules before coating of the enteric coating, and the average particle size of the granules is 600 μm to about 2500 μm.

2. The capsule according to claim 1, wherein the one or more basic inorganic salts are selected from the group consisting of basic salts of a sodium salt, a potassium salt, an aluminum salt, a magnesium salt and a calcium salt.

3. The capsule according to claim 2, wherein the one or more basic inorganic salts are selected from the group consisting of a magnesium salt and a calcium salt.

4. The capsule according to claim 1, wherein the amount of the intermediate coating layer to be coated is 0.05 part by weight to 1 part by weight on 1 part by weight of the granules containing lansoprazole or the optically active isomer thereof or the pharmaceutically acceptable salt thereof.

5. The capsule according to claim 1, wherein the amount of the enteric coating layer to be coated is 10% by weight to 50% by weight based on the total amount of the granules before coating of the enteric coating.

6. The capsule according to claim 1, wherein the core comprises at least one material selected from the group consisting of sucrose, starch, lactose and crystalline cellulose.

7. The capsule according to claim 1, wherein the enteric coating layer comprises an enteric water-soluble polymer.

8. The capsule according to claim 7, wherein the enteric water-soluble polymer is a methacrylic acid copolymer.

9. The capsule according to claim 1, wherein an average particle size of the granules is 1000 μm to 2000 μm.

10. The capsule according to claim 1, comprising lansoprazole or the optically active isomer thereof or the pharmaceutically acceptable salt thereof in an amount of 12% by weight to 40% by weight based on the total granules.

11. The capsule according to claim 1, which is a capsule for treating or preventing peptic ulcer, Zollinger-Ellison syndromes, gastritis, reflux esophagitis, symptomatic gastroesophageal reflux disease (symptomatic GERD), NUD (non ulcer dyspepsia), stomach cancer, gastric MALT lymphoma, ulcer resulting from nonsteroidal antiinflammatory medicaments, or excess stomach acid or ulcer due to post-operation stress, a preparation for eradicating *Helicobacter pylori*, or a preparation for suppressing upper gastrointestinal hemorrhage due to peptic ulcer, acute stress ulcer, hemorrhagic gastritis or invasion stress.

12. The capsule according to claim 3, wherein the basic inorganic salt is magnesium carbonate.

13. The capsule according to claim 1, which is a No. 3 to 5 capsule comprising 30 mg of lansoprazole.

14. The capsule according to claim 1, which is a No. 4 to 5 capsule comprising 15 mg of lansoprazole.

15. The capsule according to claim 1, which is a No. 1 to 3 capsule comprising 60 mg of lansoprazole or an optically active isomer (R isomer) thereof.

16. The capsule according to claim 1, which is a No. 2 to 4 capsule comprising 40 mg of an optically active isomer (R isomer) of lansoprazole.

17. The capsule according to claim 1, which is a No. 3 to 5 capsule comprising 30 mg of an optically active isomer (R isomer) of lansoprazole.

18. A pharmaceutical composition which is a combination of an antimicrobial agent and the capsule according to claim 1.

* * * * *